United States Patent [19]
Plassche, Jr. et al.

[11] Patent Number: 5,318,576
[45] Date of Patent: Jun. 7, 1994

[54] ENDOVASCULAR SURGERY SYSTEMS

[76] Inventors: Walter M. Plassche, Jr., 1209 Cloer St., Rochester, N.Y. 14610; Armin K. Weiss, 62 Stanfield Terr., Rochester, N.Y. 14619

[21] Appl. No.: 991,778
[22] Filed: Dec. 16, 1992
[51] Int. Cl.$^5$ ............................. A61B 17/32
[52] U.S. Cl. ..................... 606/159; 606/170; 606/180; 604/22
[58] Field of Search ............ 606/159, 170, 171, 180; 604/22

[56] References Cited

U.S. PATENT DOCUMENTS

| | | | |
|---|---|---|---|
| 4,895,778 | 1/1990 | Papantonakos | 606/159 |
| 5,030,201 | 7/1991 | Palestrant | 604/22 |
| 5,100,425 | 3/1992 | Fischell et al. | 606/159 |
| 5,152,773 | 10/1992 | Redha | 606/159 |
| 5,154,724 | 10/1992 | Andrews | 606/159 |
| 5,176,693 | 1/1993 | Pannek, Jr. | 604/22 |
| 5,178,625 | 1/1993 | Groshong | 606/170 |
| 5,192,291 | 3/1993 | Pannek, Jr. | 606/159 |

OTHER PUBLICATIONS

Endovascular Surgery: second edition; Samuel S. Ahn and Wesley S. Moore, editors; published by Saunders, Philadelphia, Pa.; 1992,; chapters 28-34, pp. 263-319.

Primary Examiner—Peter A. Aschenbrenner
Assistant Examiner—William Lewis
Attorney, Agent, or Firm—M. Lukacher

[57] ABSTRACT

In order to remove a lesion constricting a vascular channel, such as arteries (1), a cutter (10) of oblong, and preferably ellipsoidal shape is provided by a plurality of flexible segments (15). The segments have cutting elements (20) in the form of cusps and mounds (25) distributed over their outwardly facing surfaces. The cutter is shortened axially between its distal (D) and proximal ends to radially expand it and present the cutting elements and mounds to the lesion. The mounds help to smoothen the inside of the vascular channel following cutting of the lesion material by the cutting elements. Reaming (reciprocal movement of the cutter) along the axis (11) of the channel or rotation of the cutter may be effected from a control unit (100) via a drive shaft 40 which encases a coaxial fluid/suction supply via pipes (60, 70) to the vicinity of the cutter. A guidewire (30), which may be in a sleeve (90) is also used for axial retraction of the segments to expand the cutter. The drive shaft, guide wire and supply are in a catheter (3).

15 Claims, 5 Drawing Sheets

SMOOTH, ROUNDED, NON-CUTTING SEGMENT EDGES

SMOOTH, ROUNDED, NON-CUTTING SEGMENT EDGES

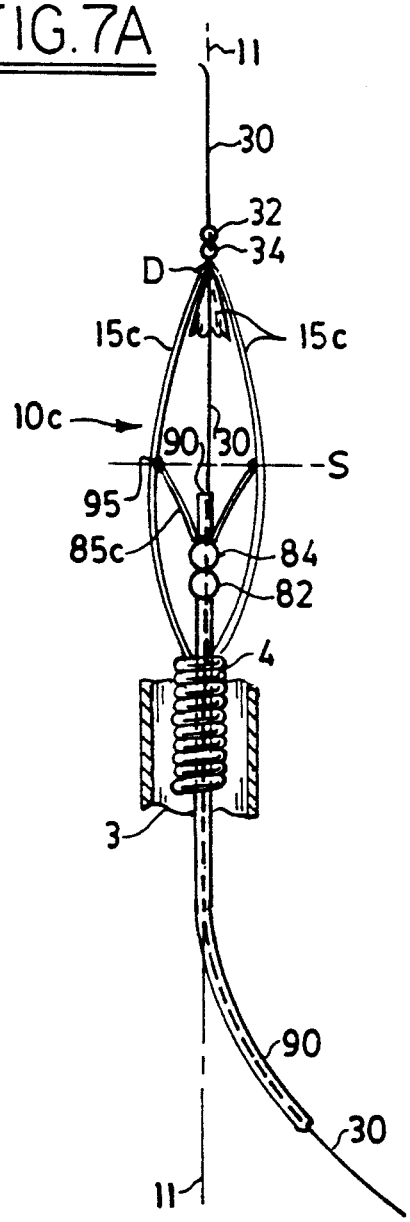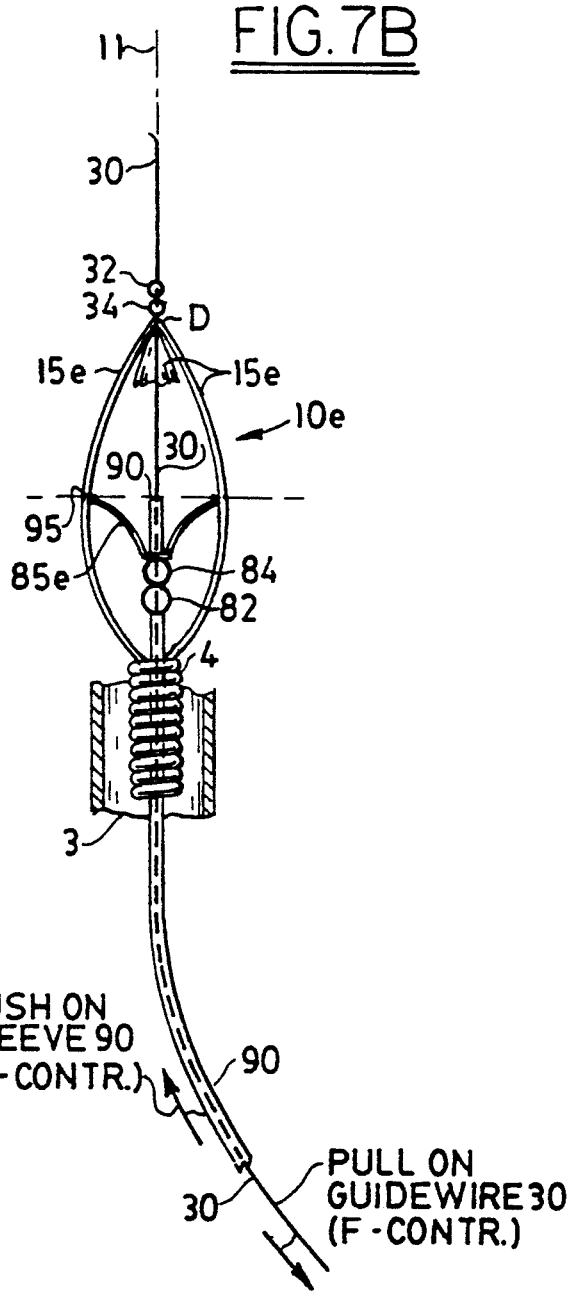

ENDOVASCULAR SURGERY SYSTEMS

FIELD OF THE INVENTION

The present invention relates to endovascular surgery systems and especially to atherectomy systems removing plaque or other deposits from the inside of human arteries, veins or vascular shunts or bypass grafts by cutting means which are advanced toward and then past a predetermined plaque zone inside an artery. More particularly, the invention relates to a cutting element for endovascular surgery having a least a cutter surface capable of selective radial expansion to facilitate maximum plaque removal in a single endovascular atherectomy procedure, requiring only one insertion of the cutter element into a vascular channel.

BACKGROUND AND FEATURES OF THE INVENTION

Balloon angioplasty and mechanical atherectomy are the two principal endovascular medical procedures which have been developed for management of lesions in the coronary, visceral, and peripheral artery trees of patients having medical conditions judged suitable for such procedures or, alternatively, of patients having medical conditions judged unsuitable for surgical artery-bypass procedures.

Briefly, in the balloon angioplasty procedure, a substantially uninflated balloon at or near the tip of a catheter system is advanced inside an artery toward a predetermined (for example, by prior radiological procedures) location within the artery, where blood flow has been restricted or curtailed by build up of plaque. Upon positioning the tip of the catheter system at the location of the lesion (depending on the medical characteristics of the lesion, a lesion is also referred to either as a stenosis or as an occlusion), the balloon is inflated to create radial (and possibly some axial) forces, directed outwardly against the lesion, thereby displacing the plaque constituting the lesion by redistributing the plaque material over a now radially expanded arterial wall (also referred to as a dilated arterial adventitia). Hence, plaque displacement by the inflated balloon results in an enlarged open channel (also referred to as the lumen) within the artery at the location of balloon intervention, thus ensuring, at least in principle, improved blood flow through this previously restricted artery at that location.

In contrast to balloon angioplasty, atherectomy procedures are aimed at cutting, grinding, ablating or vaporizing plaque or other material from lesions within arteries, veins or vascular shunts. Plaque ablation may occur predominantly by localized endovascular application of ultrasonic energy, while plaque vaporization is likely the predominant process in localized endovascular application of optical energy from a laser source.

A common feature of present mechanical cutting or grinding atherectomy devices is the fixed dimension of a selected cutter or grinder means, suitably deposed at or near the distal end of a generally coaxially arranged atherectomy system. Means for advancing or retracting the cutting or grinding devices and associated rotational drive shafts, guide wires (when used), and outermost catheter tubes to or from the predetermined location of a lesion inside an artery are provided at the outside of the patient's body, as are rotational cutter drive means (for example, a motor or a turbine driven by compressed air) and means for introducing, as into the coaxial atherectomy system, certain fluids and/or means to extract (usually by controlled suction) lesion debris cut or ground at the location of the lesion within the artery under treatment. For purposes of clarity, such coaxially arranged advancing and retracting means, rotational drive means, fluid introduction and debris-extraction means will be collectively called "coaxial supply." The terms artery, vein, vascular shunt comprehend different types of vascular channels wherein the invention is useful; i.e. the system of the invention is useful in endovascular surgery in vascular channels where one type of vascular channel is mentioned (e.g. an artery) it will be appreciated that the invention is not restricted for use in connection with only such a channel.

An overview, as well as a more detailed description of present mechanical atherectomy systems and respective procedures and clinical results can be found in *Endovascular Surgery*; second edition; Samuel S. Ahn and Wesley S. Moore, editors; published by Saunders, Philadelphia, Pa; 1992, particularly chapters 28–34, pages 263–319.

While each of the present mechanical atherectomy systems offers certain procedural advantages for specific classes of lesions (for example, relatively hard, calcified plaque or relatively soft, partially compliant or rubbery plaque), the fixed dimension of the cutter associated with each of the present atherectomy systems necessitates, in some procedures, several sequential groups of steps (insertion, cutting of plaque, and complete removal of the system from the artery under treatment), starting with the smallest-dimension cutter device and progressing through larger dimension cutter devices with each respectively associated coaxial supply. This sequential procedure is time-consuming and can result in attendant medical complications.

The invention avoids such procedures and provides a single, sequentially and selectively expandable cutter surface in a mechanical atherectomy system to facilitate maximum plaque removal at each of a potential plurality of plaque locations within one and the same artery or vein with a single endovascular insertion into that artery or vein of the cutter and its associated coaxial supply.

Present mechanical atherectomy systems also use a mechanically rigid, i.e., non-compliant cutter. Rigidity or non-compliance of a cutter may be acceptable in instances where the lesion within the artery or vein is firstly located in a relatively straight, i.e., uncurved, section of the artery or vein, and is secondly composed of essentially similar material, for example, substantially calcified deposits or substantially soft or compliant deposits. Frequently, a plurality of different lesions (different in composition and different in the degree of lesion fill factor, i.e, the extent to which a lesion occupies internal arterial volume) are found along an artery, with some lesions located in relatively straight sections of the artery and other lesions located in relatively curved sections. Rigid, non-compliant cutters of present mechanical atherectomy systems generally are not suited to effectively recanaliz an artery having such a plurality of different lesions located in said various sections of an artery. In fact, present rigid cutters can perforate through the wall of an artery or vein because they do not possess adequate self centering capability, a feature particularly important in curved section of an artery or vein.

It is a feature of the invention to provide a compliant cutter surface as part of a mechanical atherectomy system which is advantageous for lesion removal from sections of arteries or veins of straight or curved shape.

As pointed out in several chapters in the above-referenced publication, *Endovascular Surgery*, clinical outcomes of endovascular mechanical atherectomy have been improved sometimes when balloon angioplasty was performed subsequent to mechanical atherectomy, so as to redistribute any remaining lesion material somewhat uniformly along the inside of the arterial wall, and hence, to affect a wider and smoother lumen than could be obtained with either procedure alone.

Features of the invention are: (a) to provide a generally ellipsoidally-shaped compliant cutter which offers improved self-centering during endovascular cutting procedures; (b) to provide a non cutting, gentle balloon-like capability on at least a portion of the surface area of a selectively expandable compliant cutter, such that at least a partial smoothing of remaining lesion material may be affected; (c) to provide on at least first portions of the compliant cutter surface, a plurality of cutter elements, and to provide on at least second portions of the compliant cutter surface a non-cutting, gentle balloon like smoothing capability; (d) to enable the physician to select the location, frequency, distribution, size and shape of a plurality of cutter elements on at least portions of the surface of a compliant cutter, which may be on first portions of the surface; second portion of the surface being expandable to provide a non-cutting balloon-like smoothing capability; and (e) to enable the physician to select a sequentially and selectively expandable cutter surface, the degree of expansion of which is selectable by the physician.

BRIEF DESCRIPTION AND OBJECTS OF THE INVENTION

It is the principal object of the invention to provide improved systems (method and apparatus) for endovascular surgery.

Another object of the invention is an improved endovascular surgical apparatus having an expandable rotatable cutter, which is especially suitable in providing an improved mechanical atherectomy system.

A more specific object of the invention is to provide an improved surgical implement having a selectively expandable cutter surface, which is provided by partial segmentation of an unexpanded rotationally symmetrical thin-walled and hollow ellipsoidal body of surgical steel.

Briefly described, the invention in accordance with an embodiment thereof, provides an improved surgical implement having an expandable cutter with a plurality of expandable cutter segments provided by partial segments of a hollow ellipsoidal cutter body, each segment presenting cutter elements on its surface. The cutter surface is expandable by application of compressive axial force along the major axis of the ellipsoidal body. These partial segments of the hollow ellipsoidal body can be compliant. The partially segmented ellipsoidal body can be advanced endovascularly toward an arterial lesion while in its most contracted quiescent state and in a non rotating mode. The expandable cutter can be coupled to rotational drive means and to coaxial supply means for performing one or more of the functions of advancing, retracting, expanding, contracting, and rotating the cutter, and for providing fluid delivery and/or removal.

BRIEF DESCRIPTION OF THE DRAWINGS

These foregoing and other features, objects and advantages of the invention will become more readily apparent from the following description when considered in conjunction with the accompanying drawings, wherein:

FIG. 7A is an elevation view, partially in section, of a contracted atherectomy cutter having mechanical means for expanding the cutter in accordance with another embodiment of the present invention, the cutter being in its unexpanded (or contracted) state.

FIG. 7B is a view of the atherectomy cutter of FIG. 7A in its expanded state.

FIG. 8 is an enlarged perspective view of a strut assembly of the cutter shown in FIGS. 7A and B.

DETAILED DESCRIPTION OF THE PREFERRED EMBODIMENTS

Figure 1A:
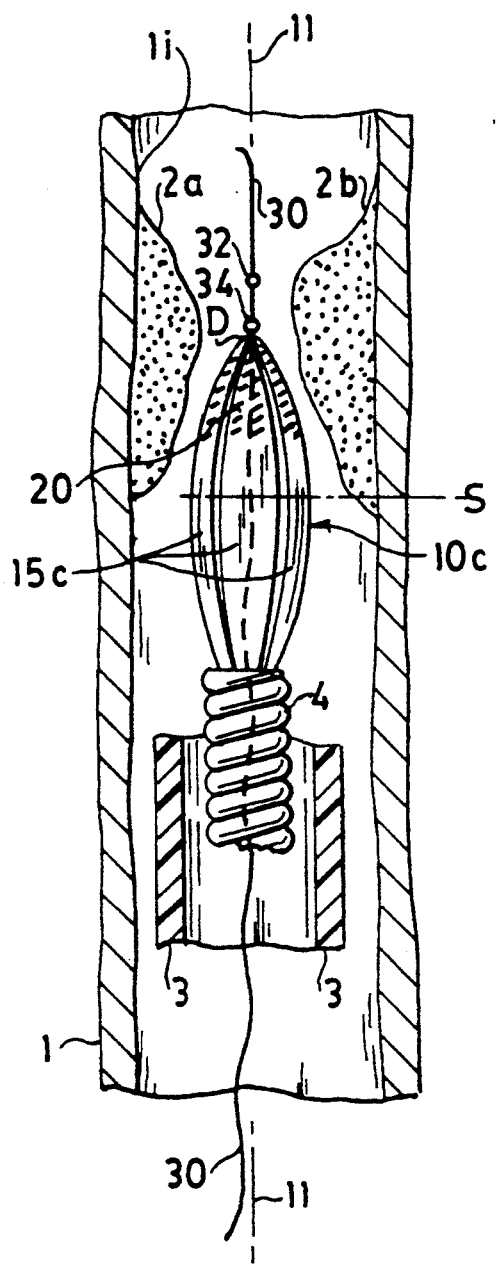
FIG. 1A is a sectional review through an artery which shows schematically an atherectomy system, in accordance with the present invention and particularly the cutter body thereof in its contracted, quiescent state near a plaque deposit inside an artery.
Figure 1B:
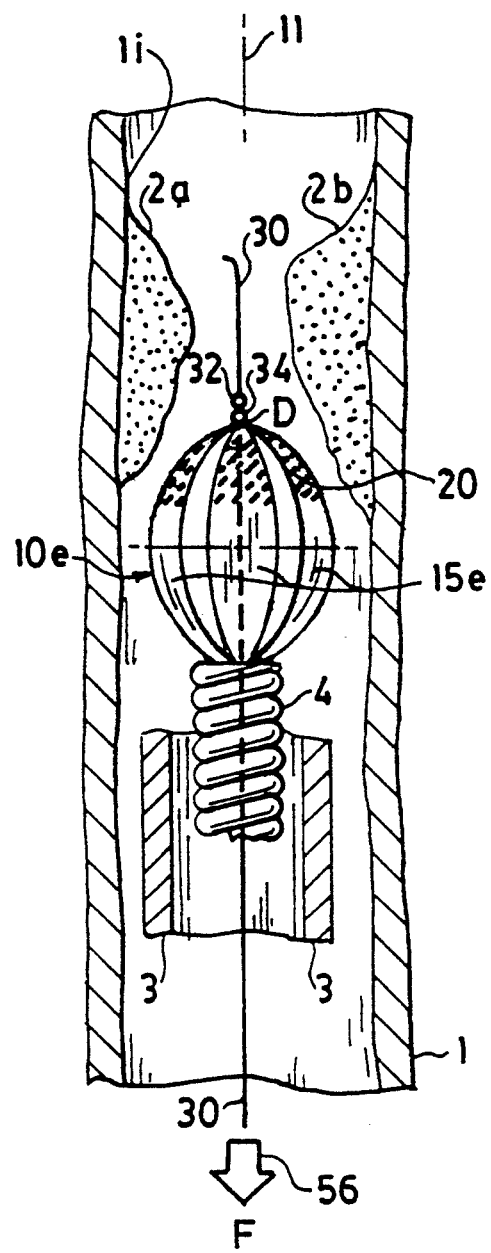
FIG. 1B is a sectional view similar to FIG. 1A which shows schematically the cutter body, in an expanded state near a plaque deposit inside an artery.
Figure 2:
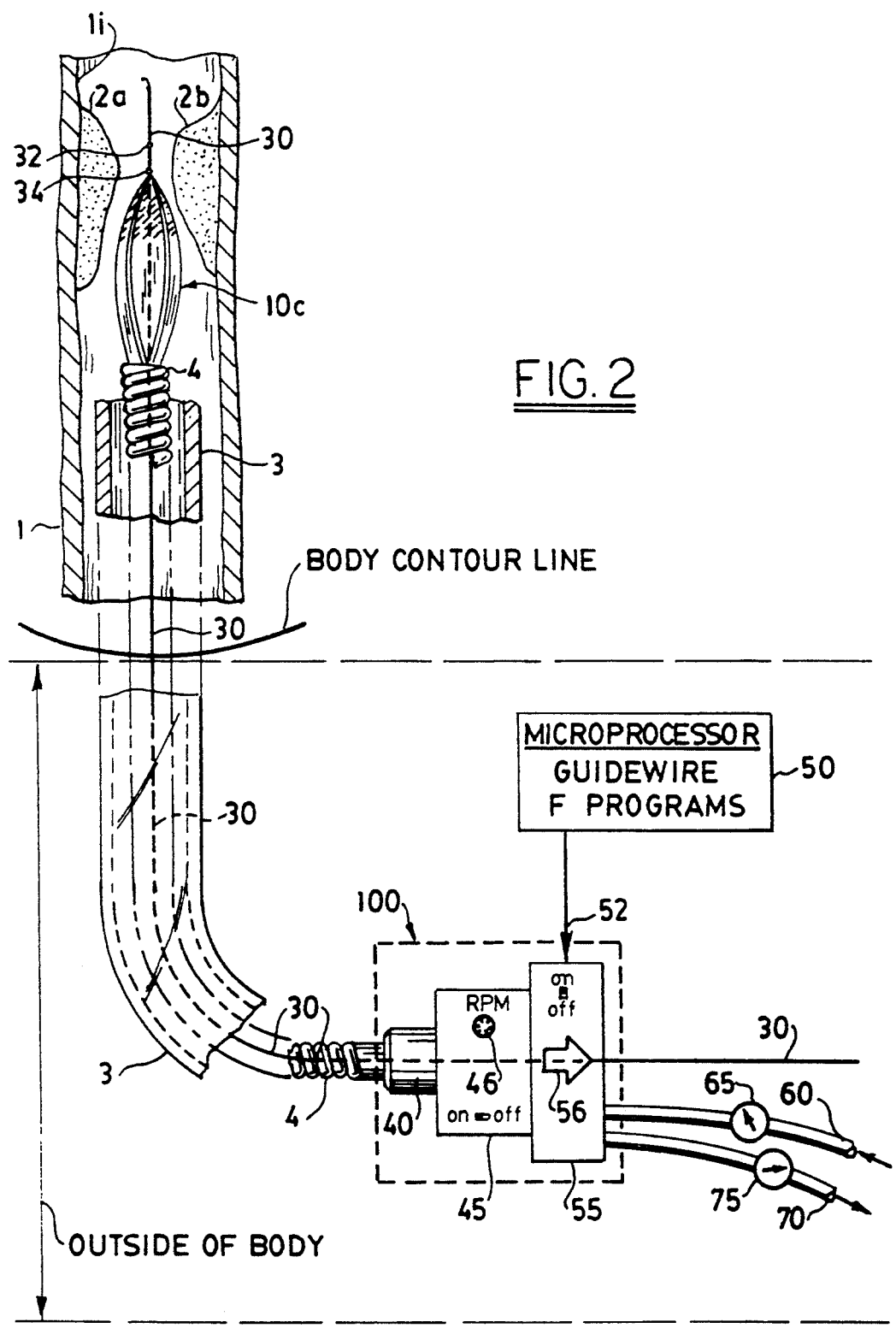
FIG. 2 is a diagrammatic view of the atherectomy system showing, schematically the body-external supply and control members for the expandable-cutter, which is shown in the artery.

Referring particularly to FIGS. 1A, 1B, and 2, there is shown schematically an artery 1 with a section of inner arterial wall 1*i* having plaque deposits 2*a*, 2*b*. Atherectomy cutter 10(*c*), depicted in its radially contracted state (c), is positioned within artery 1 in proximity to plaque deposits 2*a*, 2*b* by advancing the cutter's flexible and hollow drive shaft 4, and the guidewire 30 inside the shaft 4, along the inside of a catheter tube 3 which is inserted into an appropriate artery from the exterior of the patient's body, as indicated by the body contour line in FIG. 2. This initial positioning of cutter 10(*c*) is performed by gently advancing the compact, hand-held activator and control unit 100 (shown in dashed outline). Endoarterial positioning, advancing, and retricting motions are monitored by appropriate diagnostic procedures, for example, by fluoroscopy (with or without digital "road mapping" capability).

The activator and control unit 100 may be of conventional design except for means therein for controlling the expansion of the cutter 10. It includes a drive shaft drive unit 45 with an OFF/ON switch or lever (not shown) and a rotational speed control (rpm control) 46 to adjust rotation of the flexible drive shaft 4 throughout a preferred range of from about 50 rpm to about 1000 rpm; the speed is selected by the physician and depends on the type, location, and extent of plaque deposits 2a, 2b in artery 1, and also on the extent of expansion (or contraction) of expandable cutter 10. Drive shaft drive unit 45 is equipped with a collet or chuck 40 which connects to drive shaft 4. A guidewire 30 extends through the drive shaft and through the collet/chuck 40. The cutter is normally contracted due to spring forces internal thereof. It is expanded by pulling on the guidewire 30 using pulling means in a controller 55.

Attached to drive shaft drive unit 45 is the guidewire force (F) controller 55 and an OFF/ON switch, lever, or pedal (not shown). Guidewire force controller 55 can, for example, be a stepper motor mechanically linked to guidewire clamping/release means, for example, an electromagnetically activated guidewire collet (not shown). Guidewire force controller 55 is responsive to electrical signals provided by a microprocessor 50 through electrical connection 51. Microprocessor 50 contains a menu of programs reflective of sequences of differing guidewire forces F required for different procedures or for different conditions during one and the same procedure. The effect of guidewire force controller is to apply a tension force 56, indicated by an open arrow, on guidewire 30, relative to the structural element of flexible drive shaft 4.

Catheter tube 3, partially hollow flexible drive shaft 4, and guidewire 30 together constitute a coaxial supply system, thus providing for optional introduction of flushing fluid (liquid or gas) via a pipe 60 having a fluid regulator 65 and/or removal of fluid or lesion debris via a pipe 70 having a suction regulator 75. The pipes 60 and 70 connect a fluid/suction pump or pumps (not shown) with partially hollow drive shaft 4 and with the space between drive shaft 4 and catheter 3, thereby providing fluid and/or suction in the vicinity of the cutter.

Referring now particularly to FIGS. 1A and 1B, radially contracted cutter 10(c), extends longitudinally, backwards from a distal end D thereof. The minor axis, S, (median plane) extends radially of the cutter body. The cutter body has a plurality of cutter segments 15(c). Each cutter segment has cutter elements 20 disposed on at least a portion of the segment's surface, which faces outwardly toward the arterial wall, the surface portion extending from the forward or distal end D of the cutter surface by a distance preferably not exceeding the location of the minor axis S of the hollow, segmented, rotationally ellipsoidal cutter 10. Cutter 10(c) is shaped generally like a football, and having segments 15(c) formed by cutting or sawing the football shell along the direction of the major (long) axis of the football. Hence, each segment 15(c) has curvature along both major and minor axes, consistent with surface curvature of the football. The cutter elements 20 can be provided on the leading (in the direction of rotation) surfaces of the segments. These surfaces are defined by the outwardly facing surfaces and the longitudinal sides of the segments. The cutter elements 20 are preferably formed by projecting areas on the outwardly facing surfaces of the segments 15, as described hereinafter in connection with FIGS. 4 and 5A and B.

Figure 6:
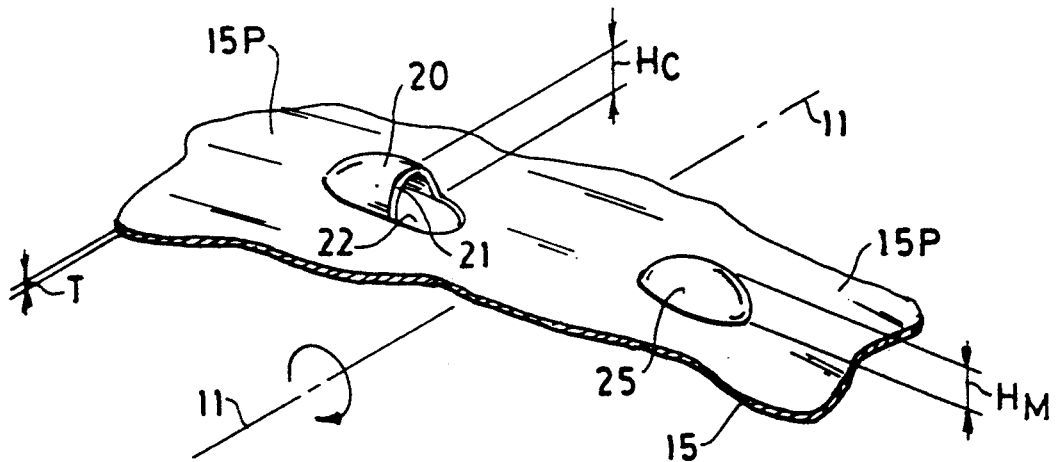
FIG. 6 is an enlarged, fragmentary, perspective view of a portion of a cutter segment surface, of the type shown in FIGS. 4, 5A and B, having a cutter element and a mound element projecting from that surface.

The expandable, football-shaped segmented cutter is made of surgical quality stainless steel sheet material of a thickness T (see FIG. 6). The thickness is selected to give the assembled segmented cutter 10(c), and upon each of its segments 15(c), mechanical compliance due to the leaf-spring like configuration of the cutter segments. The degree of mechanical compliance of expandable cutter 10(c) is selected in accordance with the tension force F which is applied on guidewire 30 with respect to flexible drive shaft 4, since it is that tension force which is used to expand the expandable cutter 10 from its normal contracted or quiescent state 10(c) to an expanded state 10(e), in a first preferred embodiment of the invention. A second embodiment for effecting cutter expansion is described in conjunction with FIGS. 7A, 7B and 8.

Figure 3:
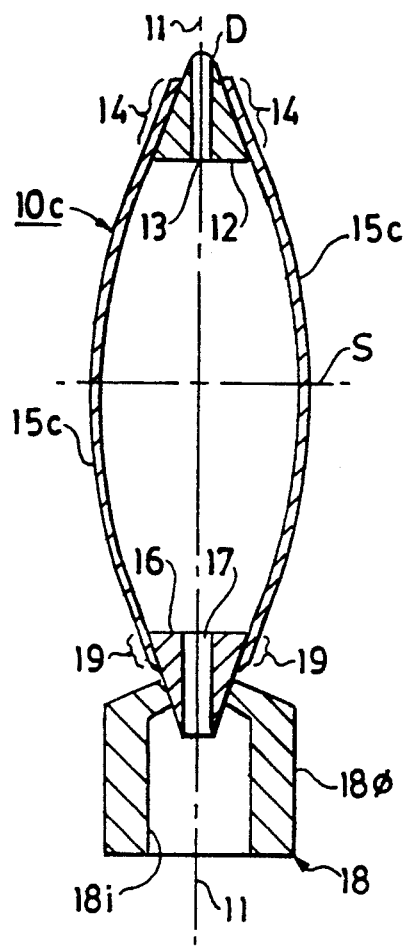
FIG. 3 is a sectional view of a cutter assembly having compliant cutter body segments attached to conical end bushings.

Guidewire 30 extends through coaxial channels 13 and 17 in bushings 12 and 16 (see FIG. 3) at each apex of the football-shaped segmented cutter 10(c) and extends beyond distal apex D. Along the guidewire extension beyond D, a first bead 32 is fixedly deposed on guidewire 30, for example, by crimping, and a second bead 34 is slidably deposed on guidewire 30. The proximal apex, opposite distal apex D, is mechanically retained by drive shaft 4 by means of a collar 18 (FIG. 3). In FIG. 1A, the absence of a guidewire force with respect to the drive shaft is indicated schematically by a slack guidewire.

Upon selection of an appropriate guidewire force program in microprocessor 50, and following activation of guidewire force controller 55, the tension (pulling) force 56 is transmitted along the guidewire 30 through unit 100 and the coaxial supply, with respect to drive shaft 4, thereby drawing fixedly positioned bead 32 against slidable bead 34, which in turn, provides peripheral and rotatable contact to apex D (i.e., a bearing surface at the tip of the bushing 12) in FIG. 1B, the tensioned guidewire 30 is indicated schematically by a taut line, occasioned by guidewire force F (open arrow designated 56). Due to the leaf spring like compliance of the cutter segments, cutter segments 15(e) are expanded radially outwardly, thereby providing a radially expanded cutter (i.e., an expanded diameter cutter 10(e).

It is not necessary that the cutter be rotating during initial cutter placement or final cutter retraction, nor during cutter expansion and cutter contraction procedures. Cutter rotation can commence upon appropriate positioning of the expandable cutter, by activation of drive shaft drive unit 45, either before or after positioning at or near the site of the deposits 2a and 2b. However, a physician may elect some cutter rotation during cutter expansion and contraction procedures by choosing an appropriate menu in microprocessor 50.

Due to the design (and especially the number and distribution of the cutter elements 20) at least part of the atherectomy procedure can be performed without cutter rotation by axial forth and back reaming motion. In such circumstances, drive shaft drive unit 45 remains turned off. Such motion may be applied normally by pulling and pushing the drive shaft 4 by manipulating the unit 100 (FIG. 2), alone or together with the catheter tube 3. A reciprocable drive in the controller 100 may alternatively be used.

FIG. 3 depicts a cutter assembly 10(c) with cutter segments 15(c) with the distal end cone-shaped bushing 12 having the coaxial channel 13. The bushing supports the cutter at its distal end, and rotatable bead 34. It also receives the guidewire 30 in rotatably axially slidable relationship allowing the guidewire 30 (not shown) to project beyond distal apex D. At the opposite, proximal cutter apex, along major axis 11, is shown the second cone-shaped bushing 16 having an enlarged coaxial channel 17 suitable for removing fluid and lesion debris via suction. Bushings 12 and 16 can be of different dimensions and of different cone angles, depending on the desired shape of the assembled cutter. The collar 18 is attached to the lower end bushing 16. Collar 18 has an inner surface 18i and an outer surface 18φ. Surface 18i is, for example, connected to drive shaft 4 and outer surface 18φ can be slidably connected to the inside of the catheter tube 3. Attachment of drive shaft and catheter tube to surfaces 18i and 18φ, respectively, can be effected by, for example, suitable twist-lock connectors 20 (not shown), clamping means (not shown), or fitting over gaskets or O-rings (not shown). Of course, if catheter tube 3 is attached to collar 18, it must be attached slidably to avoid rotation of catheter tube 3.

Cutter segments 15(c) are fixedly attached to cone shaped bushing surfaces along surface portions 14 and 19, respectively. Such attachment can be achieved by, for example, spot-welding or brazing. The number n of cutter segments 15 assembled around cone-shaped bushings 12, 16 depends upon the geometrical shape and size of the cutter segments. For example, if relatively narrow width, strip shaped cutter segments are assembled in a cutter assembly, n can be as high as 6. If relatively broad-width, ellipse shaped cutter segments are assembled in a cutter assembly, n can be as low as 2. An atherectomy cutter preferably has at least n=2 cutter segments 15 assembled in radial symmetry with respect to major axis 11 of the body defined by the segments.

Figure 4:
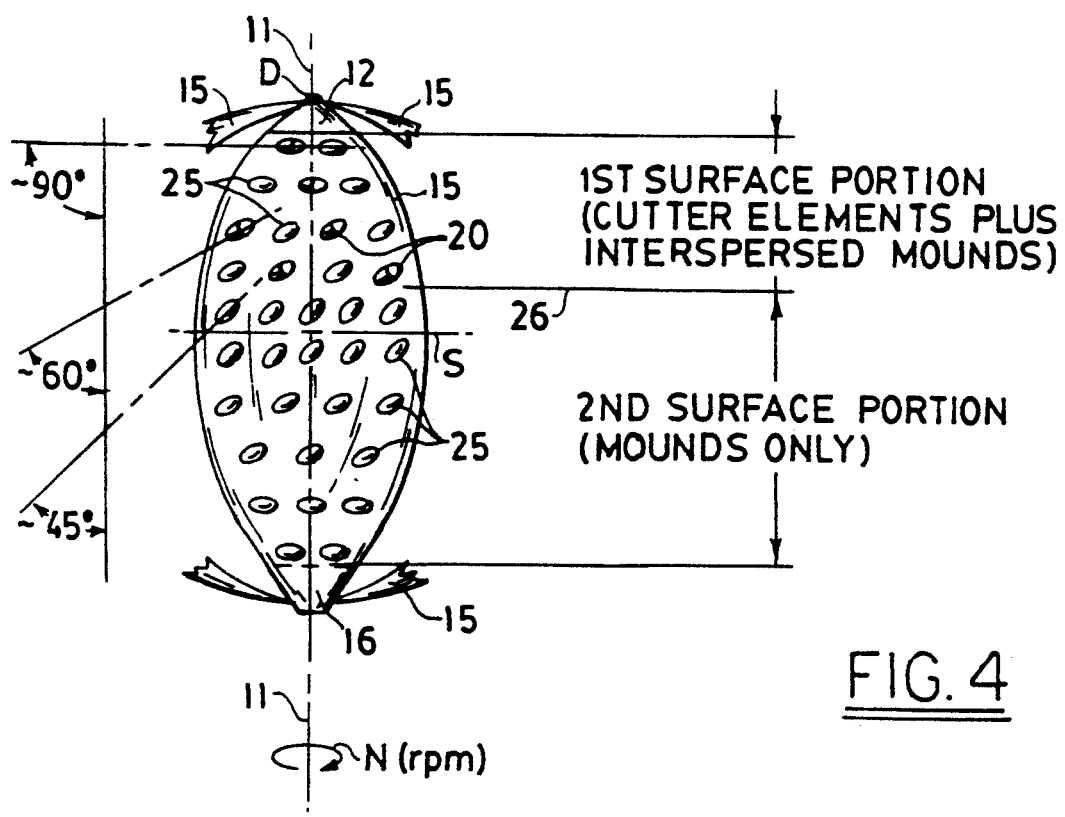
FIG. 4 is a fragmentary elevational view which depicts an ellipsoidal segment of a cutter having cutter elements and non-cutting mounds in a first surface portion, and mounds only in a second surface portion, in accordance with another embodiment of the present invention.

With particular reference to FIGS. 4–6, there are shown schematically preferred embodiments of cutter elements 20 and of non-cutting mounds 25 interspersed or distributed among the cutter elements 20 along first surface portions extending from distal cutter apex D by a distance preferably not exceeding the location of the minor or short axis S (median plane) of ellipsoidal or football shaped cutter 10.

Enlarged cusps (projections) provide the cutter element 20 and non-cutting mounds 25, both project upwardly above a cutter segment plane 15P defined by the outwardly facing surface of a cutter segment 15 (see FIG. 6). A surgical-quality stainless steel sheet material of thickness T is shown to have been pre-formed into a cutter segment 15, so as to exhibit two dimensional curvature and smooth, rounded, non-cutting segment edges. It is preferable that cutters in accordance with the present invention provide cutting actions only by their cutter elements 20 and not by the edges of respective cutter segments. This avoids possible tearing into the walls of the artery by the flexible segment edges, and facilitates axial reaming without rotation of the cutter 10.

Cutter element 20 is generally a semi ellipsoidal or spherical upward protrusion or projection of cutter segment sheet material to an altitude (height) $H_c$ above cutter plane 15P. Protruding cutter element edge 21 is sharpened (formed into a blade). Preferably it has monotonic curvature emanating from, and returning to, plane 15P after passing through $H_c$. Beyond cutter edge 21 is a cut-out 22 extending through the thickness T of cutter segment 15. Cut out 22 is intended to facilitate passage of cut lesion or plaque material toward the inside volume of cutter 10, from where it can be suctioned off via concentric channel 17 in conical bushing 16, for example through partially hollow drive shaft 4 by suction means 70, as shown in FIGS. 2 and 3.

In FIG. 6, one of the mounds 25 is shown projecting upwardly above cutter segment plane 15P by maximum indicated height $H_m$. Cutter element height $H_c$ and mound height $H_m$ can differ or they can be identical. Mounds 25 are closed-surface, smooth protrusions intended to modify the cutting efficacy of cutter elements 20 and also to assist in smoothing remaining (uncut) plaque material continuously along the arterial wall in proximity to the respective position or location of the cutter elements 20. In this way the mounds provide gentle smoothing of remaining lesion material, thereby smoothing the enlarged vascular channel.

Cutter elements 20 and non-cutting mounds 25 can be formed in conjunction with, or separately from, the curve-shaping (stamping) of a cutter segment from metal sheet material. Forming and shaping cutter segments, as well as cutter elements and sharpening of cutter edges 21, and rounding and smoothening of edges of cutter segments 15, may be carried out with tools and procedures suitable for the relatively small size of endovascular cutters. For example, electroplating, electrode-less plating, chemical milling, photolithographic techniques and micro-machining procedures with optical lasers may be suitable means for fabrication of expandable cutters and their constituent parts.

Figure 5A:
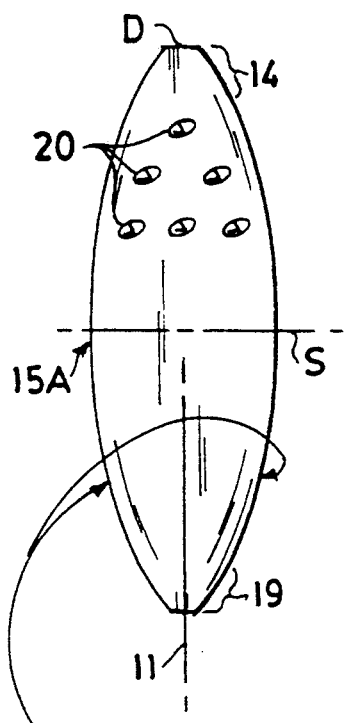
FIG. 5A is a top view of an ellipse shaped cutter segment of a cutter assembly, in accordance with still another embodiment of the present invention.
Figure 5B:
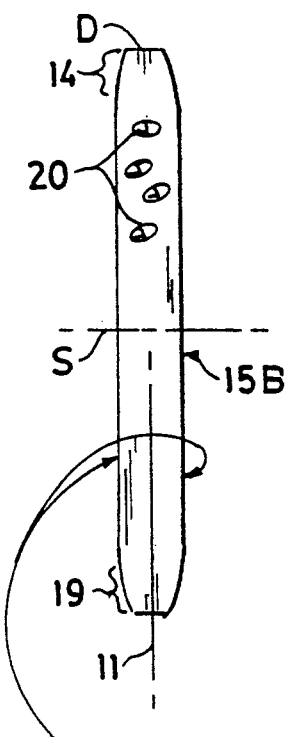
FIG. 5B is a top view of a strip shaped cutter segment of a cutter assembly, in accordance with still another embodiment of the present invention.

FIGS. 5A and 5B depict an example of an ellipsoidally shaped cutter segment 15A and of a generally rectangular, oblong or strip shaped cutter segment 15B, respectively. As pointed out previously, the selection of the shape of a cutter segment depends upon the intended application of the cutter. Only cutter elements 20 are indicated although mounds may also be used. Dimension 14 near distal ends D, and lengths 19 near the opposite (proximal) ends of cutter segments 15A and 15B, reflect identically labeled dimensions in FIG. 3.

FIG. 4 shows one ellipsoidal cutter segment 15 in full and fragments of two adjacent segments. These have distributed over a first or forward (near the distal end) surface portion both, cutter elements 20 and mounds 25, while only mounds are distributed throughout a second surface portion near the proximal end of the segments. The first surface portion can extend from near the distal end D along major axis 11 to within about 20% of the surface distance between D and the minor axis S to a line indicated at 26. Preferably, the cutter elements 20 do not extend beyond minor axis S. The second surface portion (mounds only) extends from line 26 to the end opposite the end D (the proximal end) along the surface of cutter segment 15.

With respect to major elliptical (or football) axis 11, cutter elements 20 and mounds 25 are shown to vary in angle of inclination from an angle of about 90° to axis 11 near the apex zones to about 45° near the minor axis S. This configuration provides for less aggressive cutter (and mound) angles in the central zone, where the peripheral velocity (at a selected rotational frequency of N rpm about major axis 11) is the highest, while providing maximum cutter angles near apex D, where the peripheral velocity is lower.

Cutter elements 20 over a first surface portion, which preferably does not exceed one half of the total surface area of cutter segments 15, is aimed at providing cutting action substantially only in the forward direction, i.e., in the distal direction of axial cutter translation, and not upon retraction of the cutter. Furthermore, this configuration is considered to afford some "balloon like" smoothing of remaining plaque as the radially widest portion (the minor axis S) of the cutter surface passes by the arterial location where plaque removal has just occurred.

In certain plaque removal cases, it may be desirable to replace mounds 25 entirely by a uniformly polished second surface portion in a cutter having cutter elements 20 and mounds 25 distributed only over a first surface portion. And it can be advantageous to extend distribution of cutter elements 20 from distal end D to minor axis S of a cutter segment 15, particularly when lesion material is predominantly soft or rubbery in consistency. Furthermore, cutter elements 20 can vary in cusp height $H_c$ of cutting cusps 21 on a cutter segment 15, thereby providing another option to the physician to select an expandable cutter with particular cutting features, which can be desirable in particular endovascular atherectomy procedures.

FIGS. 7A, 7B, and 8 depict a second embodiment of an expandable cutter of an atherectomy system. Here the flexible drive shaft 4 is no longer used to transfer both rotational and axial forces between activator and control unit 100 and cutter 10. Rather, flexible drive shaft 4 conveys only rotational force to cutter 10, thereby ensuring maximum retained flexibility of flexible drive shaft 4 in atherectomy procedures where maximum flexibility of the coaxial supply means is desirable. Axially directed forces (tension and compression), required for expansion and contraction of cutter 10, are provided in this embodiment by a sequential and incremental push pull action between guidewire 30 and a flexible coaxial sleeve 90 which slidably encases guidewire 30. Sleeve 90 can be, for example, a flexible plastic sleeve made of NYLON ®, or it can be flexible wire coil sleeve. The controller 55 may be used to provide sequential and incremental push pull action between sleeve 90 and guidewire 30. The associated force programs in microprocessor 50 associated with the controller provide the sequence of actions. For example, force controller 55 may contain activatable collets, one for clamping or releasing sleeve 90 and the other for clamping and releasing the guidewire 30. Also, each collet, while in the clamping mode, is associated with an axial advancing means, for example, a stepper motor, which, in turn, is activated by electrical signals from the microprocessor 50 connecting lead 51. (FIG. 2). Sequential and incremental application of a compressive "push" force to sleeve 90, followed by intervening incremental application of a tension "pull" force to guidewire 30, are applied in an axial direction from the activator and control unit 100 to cutter 10.

As discussed above in connection with FIGS. 1A and 1B, in FIGS. 7A and B, the expandable cutter 10 is designated at 10(c) in its normal contracted, quiescent state (FIG. 7A), and it is designated 10(e) in an expanded state (FIG. 7B).

To expand the cutter 10, there is provided a strut unit 85 (see also FIG. 8), generally in the form of a spider and having leaf-spring-like struts 86 projecting from strut assembly base 88. (FIGS. 7A and 7B show only two struts for clarity of presentation, while FIG. 8 is drawn to show three struts about 120° apart, as is preferred.) Each strut end 87 is attached to the inside of one corresponding cutter segment 15 at a connecting point 95 positioned approximately in the plane of minor elliptical (or football) axis S of the contracted cutter 10(c). The attachment may be by a weld or notches may be formed in the inside surface of the segments which receive the strut ends 87. Strut assembly base 88 is rotatably and slidably deposed on sleeve 90 through concentric opening 89, and is contacted by bead 84 which is slidably positioned on sleeve 90 as well. Bead 82 is fixedly deposed on (attached to) sleeve 90, for example, by crimping. Thus, beads 82 and 84 on sleeve 90 are functionally equivalent to beads 32 and 34, respectively, on guidewire 30.

For example, if the first incremental axial force transferred from force controller (modified) 55 is a compressive "push" force on sleeve 90 (while guidewire 30 is clamped by controller 55), crimped bead 82 will tend to be pushed, together with sleeve 90, in the direction toward distal end D of cutter 10 along major axis 11, thereby pushing bead 84 and strut assembly base 88 in the same direction. The leaf-spring-like struts 86 will transfer a portion of this axial push-force to each associated compliant cutter segment 15, thus affecting incremental radial expansion of cutter 10. Sleeve 90 is now clamped by its collet in force controller 55. Microprocessor 50 may then initiate an incremental axial motion of the (clamped) guidewire collet in force controller 55, thereby incrementally increasing tension "pull" force on guidewire 30. Guidewire beads 32 and 34 transfer this guidewire tension to the distal end D of expandable cutter 10, thus effectively "moving" distant end D in the direction toward strut assembly 85 along major axis 11, and thereby affecting a corresponding incremental radial expansion of cutter segments 15, and hence, of cutter 10. The cutter 10 may be rotated by rotatably driving the flexible shaft 4.

The number of alternating incremental push-pull axial force transfers between force controller (modified) 55 and respective crimped beads 82 and 32, respectively, influences the time required to, for example, achieve a fully expanded-state cutter when starting with a fully contracted-state cutter. Additionally, depending on the particular nature, composition, location and extent of a lesion or plaque deposit inside an artery, either gradual or rapid cutter expansion and/or contraction may be indicated while performing the atherectomy procedure with the selectively expandable cutter atherectomy system of the present invention.

From the foregoing description it will be apparent that an improved system for endovascular surgery has been provided. Variations and modifications of the system, the cutter element, thereof and the control mechanism and electronics therefor, within the scope of the invention will undoubtedly suggest themselves to those skilled in this art. Accordingly, the foregoing description should be taken as illustrative and not in a limiting sense.

We claim:

1. Apparatus for endovascular surgery, including atherectomy, comprising:

(a) an expandable and ellipsoidal hollow cutter body having a plurality of flexible segments with smooth segment edges arranged to form said body in a first ellipsoidal shape along a major ellipsoidal axis extending longitudinally between a distal end and a proximal end of said body, said ellipsoidal body having a minor ellipsoidal axis bisecting said cutter body between said distal and said proximal ends;

(b) cutting elements disposed on at least a portion of an outwardly facing surface of each one of said plurality of flexible segments;

(c) smoothing mounds distributed on said outwardly facing surface of each of said segments;

(d) means for compressing said flexible segments along said major ellipsoidal axis between aid distal and proximal ends to expand said cutter body in another ellipsoidal shape and present said cutting elements and said mounds to lesion material to be excised from within a vascular channel; and (e) means for moving said cutter body to affect cutting action on said lesion material by said cutting elements.

2. The apparatus according to claim 1, wherein each one of said plurality of flexible segments is a strip of resilient sheet material having spring characteristics which urge said ellipsoidal body to said expandable state having said first ellipsoidal shape.

3. The apparatus according to claim 2, wherein said cutting elements are provided by a plurality of cusps projecting from said at portion of said outwardly facing segment surfaces, said cusps having curved blade edges.

4. The apparatus according to claim 3, wherein said cusps are distributed on each of said outwardly facing segment surfaces between said distal end of said cutter body and said bisecting minor ellipsoidal axis, said curved blade edges of said cusps nearer to said distal end being oriented closer to a perpendicular to said major ellipsoidal axis than curved blade edges of cusps farther from said distal end and closer to said minor elliptical axis.

5. The apparatus according to claim 4, wherein said smoothing mounds are distributed on said outwardly facing surface of each of said segments between said distal and said proximal ends of said cutter body for providing a smoothing action against the just cut lesion.

6. The apparatus according to claim 1, wherein said means for compressing said segments along said major ellipsoidal axis includes a wire extending through said cutter body and beyond the distal end thereof and engageable with said distal end when retracted.

7. The apparatus according to claim 6, wherein said means for compressing said segments along said major ellipsoidal axis further comprises a spider having a plurality of flexible struts connected to a base, a sleeve around said wire movable with respect to said base for flexing and extending outwardly said struts, each of said struts being connected to a different one of said plurality of flexible segments on the inside thereof.

8. The apparatus according to claim 1, wherein said means for moving comprises a flexible drive shaft connected to the proximal end of said cutter body, and means for rotating said flexible shaft to rotate said cutter body about said major ellipsoidal axis.

9. The apparatus according to claim 1, wherein said means for moving comprises a flexible drive shaft connected to the proximal end of said cutter body, and means for reciprocating said flexible shaft in a forth-and-back reaming motion to reciprocate said cutter body forth and back in the direction of said major ellipsoidal axis.

10. The apparatus according to claim 1, further comprising means for providing a selectable sequence of successively greater compression of said flexible segments so that a successively greater expansion of said cutter body is achieved.

11. A method of endovascular surgery, including atherectomy, comprising the steps of:

(a) inserting a segmented expandable hollow cutter body of a first ellipsoidal shape into a vascular channel having lesion material;

(b) expanding the cutter body by compression int he direction of a major axis of the ellipsoidal shape of the segments having smooth segment edges from said first ellipsoidal shape to another ellipsoidal shape to present a cutting surface of the cutter body t the lesion; and (c) moving the cutter body of the other ellipsoidal shape with respect to the channel to separate the lesion material form the channel.

12. The method according to claim 11, wherein said expansions step includes the step of sequentially and successively compressing said segments in a direction longitudinally thereof and along said channel so as to expand said cutter body to a successively greater diameter.

13. The method according to claim 11, wherein said moving step includes the step of reciprocating said cutter body in a longitudinal direction parallel to a major axis of said other ellipsoidal shape.

14. The method according to claim 11, wherein said moving step includes the step of rotating said ellipsoidal cutter body.

15. The method according to claim 11, wherein said expansion step further includes the step of presenting to said lesion a plurality of cutting elements and smoothing mounds disposed on an outwardly facing surface of each of the segments.

* * * * *